United States Patent [19]

Schwartz

[11] Patent Number: 4,857,451
[45] Date of Patent: Aug. 15, 1989

[54] METHOD OF COMPENSATING AND CALIBRATING A FLOW CYTOMETER, AND MICROBEAD STANDARDS KIT THEREFOR

[75] Inventor: Abraham Schwartz, Durham, N.C.

[73] Assignee: Flow Cytometry Standards Corporation, Research Triangle Park, N.C.

[21] Appl. No.: 128,786

[22] Filed: Dec. 4, 1987

Related U.S. Application Data

[63] Continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.⁴ ..................... G01N 53/00; G01N 31/00
[52] U.S. Cl. .......................................... 435/7; 436/10; 424/3
[58] Field of Search ............... 436/10, 19, 800; 435/7; 526/273, 320, 328, 328.5, 181, 201, 88, 332; 424/3; 523/202, 205, 201, 223; 525/327.3, 330.3, 330.5, 343, 351, 379, 382, 384, 284, 350; 524/461, 464, 558, 853, 458; 428/407, 516, 402; 252/301.35, 408.1; 521/60, 149; 250/461.2; 356/39

[56] References Cited

U.S. PATENT DOCUMENTS

| 4,609,689 | 9/1986 | Schwartz et al. | 526/909 |
| 4,694,035 | 9/1987 | Kasai et al. | 526/201 |
| 4,698,262 | 10/1987 | Schwartz et al. | 526/201 |
| 4,699,826 | 10/1987 | Schwartz et al. | 526/201 |
| 4,699,828 | 10/1987 | Schwartz et al. | 526/201 |
| 4,714,682 | 12/1987 | Schwartz | 436/10 |
| 4,751,188 | 6/1988 | Valet | 436/10 |

Primary Examiner—Barry S. Richman
Assistant Examiner—T. J. Wallen
Attorney, Agent, or Firm—Steven J. Hultquist

[57] ABSTRACT

A kit of highly uniform microbead standards for flow cytometer alignment, compensation, and calibration, comprising a blank and/or auto-fluorescent microbead population, together with two or more series of calibrated microbead populations which match the fluorescence spectra of labeled samples to be measured on the flow cytometer. Also disclosed is a corresponding method to align, compensate, and calibrate a flow cytometer so as to make measurements on corresponding samples comparable and independent of the specific instrument and instrument settings.

22 Claims, 2 Drawing Sheets

Fig. 6

METHOD OF COMPENSATING AND CALIBRATING A FLOW CYTOMETER, AND MICROBEAD STANDARDS KIT THEREFOR

CROSS-REFERENCE TO RELATED APPLICATIONS

This application is a continuation-in-part of U.S. application Ser. No. 06/805,654 filed Dec. 11, 1985, issued Sept. 27, 1988 as U.S. Pat. No. 4,744,189, which in turn is a continuation-in-part of U.S. application Ser. No. 06/685,464 filed Dec. 24, 1984, issued Aug. 30, 1988 as U.S. Pat. No. 4,767,206.

BACKGROUND OF THE INVENTION

1. Field of The Invention

This invention relates generally to a method for aligning, compensating, and calibrating a multiple fluorescent channel flow cytometer, and to a kit of fluorescent microbeads useful for such method.

2. Background and Description of the Art

Flow cytometers are instruments which analyze biological cells and particles in a thin stream of fluid intersected by an illumination source, usually a laser beam, with the resulting forward and right angle scattered and fluorescent light analyzed with photomultiplier tubes (PMTs). Fluorescent channels are usually indicated by the designations F11, F12, F13, etc., depending on the number of channels in the instrument. Each fluorescent channel is set with barrier filters to detect a selected specific dye while filtering out all others. The channel in which a specific dye is predominantly detectable may be referred to as its primary fluorescent channel while other fluorescent channels may be designated as secondary channels.

In order to obtain accurate and reproducible results, flow cytometers must be aligned and calibrated. When operating with more than one fluorescent dye, the instrument also requires compensation for the fluorescence PMTs. Alignment, compensation, and calibration ensure that the instrument will operate at its maximum efficiency, as well as achieving reproducibility such that data taken over time or with various instruments will be comparable.

Figure 1:
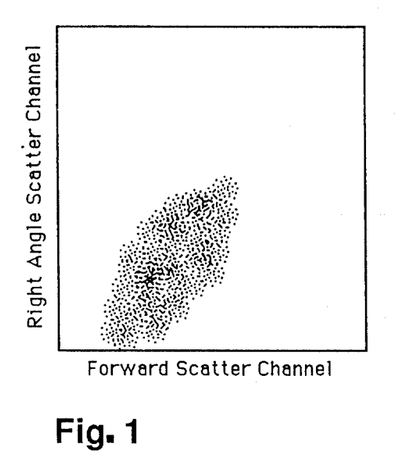
FIG. 1 is a forward versus right angle dot plot for a flow cytometer which is not aligned.
Figure 2:
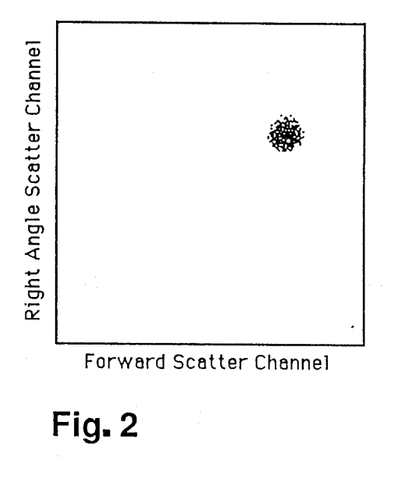
FIG. 2 is a forward versus right angle dot plot for a flow cytometer which is aligned.

Alignment is the process of adjusting and focusing the various optical and electrical components such that scatter d fluorescence signals are tuned to their highest intensity and tightest distribution, i.e., lowest coefficient of variation (CV) of the distribution. The components of the flow cytometer to be aligned include the laser, lenses, mirrors, barrier filters, and PMTs. FIG. 1 shows what the dot plot of the forward and right angle scatter channels typically looks like when the instrument is not aligned. The corresponding dot plot of FIG. 2 indicates proper alignment of those channels.

Figure 3:
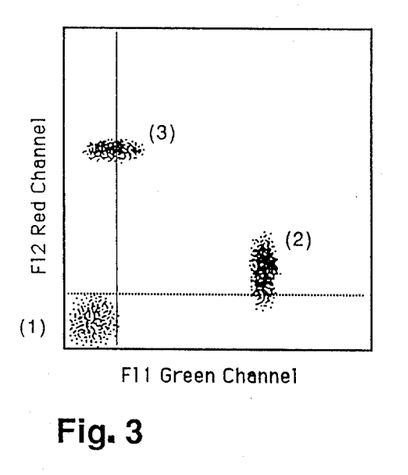
FIG. 3 is a dot plot of the green fluorescence channel F11 versus the red fluorescence channel F12 of a flow cytometer with its compensation circuits turned off. Dot populations (1) represent blank microbeads, (2) green fluorescent microbeads, and (3) red fluorescent microbeads, as do the same parenthetic numbers in FIGS. 4-5.
Figures 4, 5, 6:
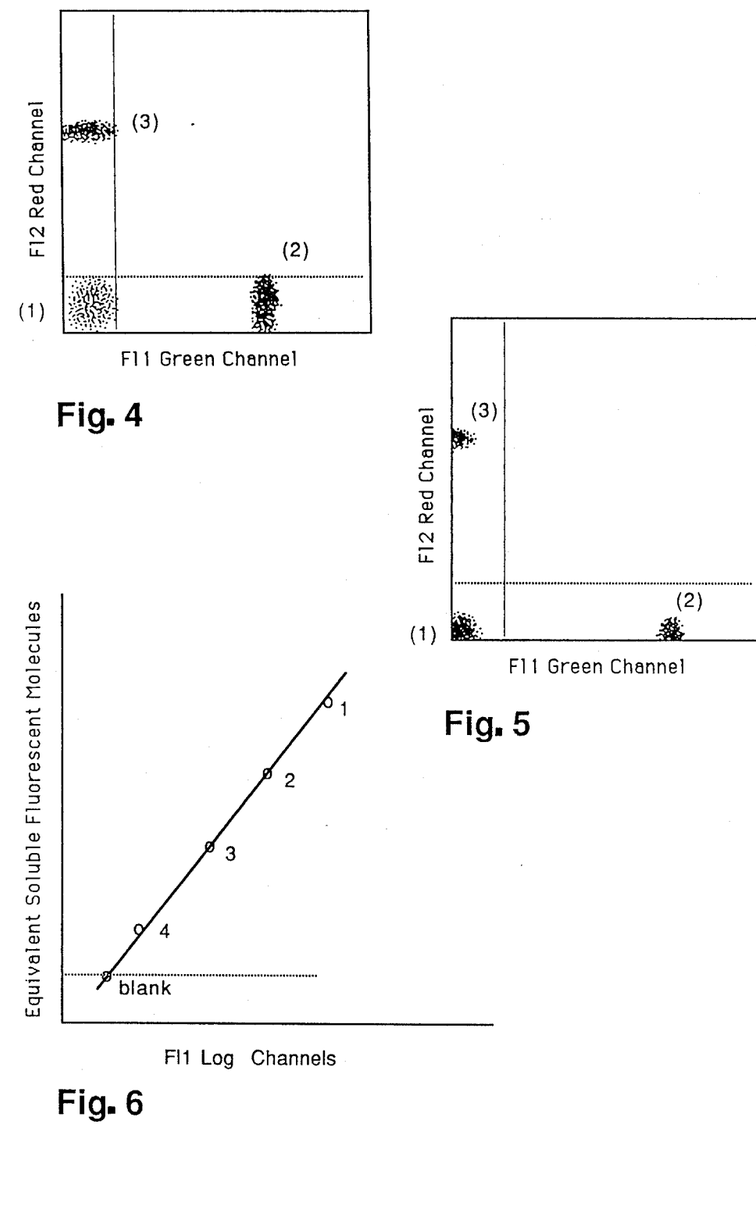
FIG. 4 is a dot plot of the green fluorescence channel F11 versus the red fluorescence channel F12 of a flow cytometer with its compensation circuits turned on and properly adjusted.
FIG. 5 is a dot plot of the green fluorescence channel F11 versus the red fluorescence channel F12 of a flow cytometer with its compensation circuits adjusted too high, resulting in loss of data from the samples being measured.
FIG. 6 is a calibration plot of the green fluorescence channel F11 of a flow cytometer, wherein numbers 1-5 indicate modal peak channels of microbead populations of decreasing fluorescence intensity, and the blank microbead indicates the sensitivity level of the instrument in that channel.

Compensation is the process of electronically removing residual signals from fluorescent dyes in secondary fluorescence channels due to spectral overlaps not removed by the barrier filters for the respective channels. When compensation circuits are turned off, the dot plot for the fluorescent channel F11 versus the fluorescent channel F12 appears as in FIG. 3 with the fluorescent microbeads (2) and (3) overlapping the boundaries designated by the blank microbeads (1). The dot plot of FIG. 4 shows that the compensation circuits are adjusted properly so that the intensity of any signal in the secondary fluorescent channels is equivalent to the blank samples. In other words, the dot group must be aligned with a blank or unlabeled sample in the secondary fluorescence channel. If this is not accomplished, the samples labeled with a single fluorescent dye will be counted in both fluorescent channels when it should only be counted in its respective primary fluorescent channel. In addition, if the compensation is set too high, as illustrated in FIG. 5, then data from the sample may be lost.

Calibration of a flow cytometer with proper standards ensures that the results from samples will be comparable over time and between different instruments. For the calibration of the intensity of fluorescence signals to be independent of the specific instrument and instrument settings, the excitation and emission spectra of the calibration standards and of the samples being measured must be equivalent and the measurements on each must be made under the same instrument settings. In addition, as described in U.S. Pat. Nos. 4,714,682; 4,767,206; and 4,774,189, and copending U.S. application Ser. No. 109,214, the disclosure of which are hereby incorporated by reference, when the calibration is made in terms of number of equivalent soluble fluorescent molecules, such correction factors as quenching and changes in extinction coefficient due to conjugation to other molecules, need not be taken into consideration.

Fluorescence calibration curves for flow cytometers may be constructed by plotting the mean or modal channels of the fluorescence intensity histograms of fluorescence microbead standards against the calibrated values of the number of equivalent soluble fluorescent dye molecules for the respective microbead standards, as shown in FIG. 6.

Small (0.1–2 microns) highly uniform microbeads are readily commercially available from a number of manufacturing companies, e.g., Seragen, Inc., Polysciences, Inc, and Interfacial Dynamics Corp. Production of large (2–50 microns) highly uniform microbeads are described in U.S. Pat. Nos. 4,247,434 and 4,336,173. The synthesis of fluorescent microbeads is taught in U.S. Pat. Nos. 4,157,323 and 4,179,685, but these microbeads are not intended to be used as uniform standards and their spectra are not designed to match those of labeled samples.

The aforementioned U.S. Pat. Nos. 4,714,682; 4,767,206; and 4,774,189, and copending U.S. application Ser. No. 109,214 relate to calibration of flow cytometers in terms of equivalent soluble fluorescent dye molecules with standards (calibration microbeads) that have matching fluorescent properties.

A kit of microbeads that match labeled cells is commercially available under the trademark CaliBrites from Becton Dickinson & Co., (Mountain View, Calif.) which consists of three microbead populations: (i) an unlabeled population, (ii) a fluorescein-labeled population, and (iii) a phycoerythrin-labeled population. None of these microbeads are calibrated in any way, and they are intended only for alignment and compensation of a flow cytometer.

It is therefore an object of the present invention to provide a method for alignment, compensation, and calibration of a flow cytometer, enabling it to operate at high efficiency with respect to fluorescence data generated thereby, and in a manner achieving reproduceability of data which is independent of specific instrument and time-frame of the data measurement.

It is another object of the invention to provide a microbead standards kit for carrying out such alignment, compensation, and calibration method.

Other objects and advantages of the invention will be more fully apparent from the ensuing disclosure and appended claims.

SUMMARY OF THE INVENTION

The present invention relates to a method of aligning, compensating, and calibrating a flow cytometer, and a kit useful for carrying out such method which contains several series of highly uniform microbeads (i.e., ≦2% coefficient of variation of diameter) which have fluorescence spectra that match the cell or particle samples to be measured, wherein the microbeads are labeled with two or more fluorescent dyes. Each series of microbeads is labeled with a specific fluorescent dye, so that the kit provides several populations of each microbead set calibrated at different fluorescence intensities. With such kit, each series of microbeads may be used to align, compensate, and calibrate its respective primary fluorescence channel of the flow cytometer. The general size and fluorescence properties of the individual microbead populations of these series of microbeads are described in U.S. Pat. Nos. 4,714,682; 4,767,206; and 4,774,189. The specific fluorescence properties of the "blank" microbead, as well as the doubly labeled microbeads included in the microbeads standards kit of the present invention, will be described more fully hereinafter.

When used separately or in combinations, the microbead populations in this kit will allow the flow cytometer to be aligned (due to the high uniformity of the microbeads), compensated (due to the matching emission of the microbead standards and the cell or particle samples to be measured), and calibrated (due to the specific levels of fluorescence intensity of the microbeads in terms of number of equivalent soluble fluorescent dye molecules). These operations will enable the instrument to yield accurate reproducible data so that fluorescence intensity measurements made thereafter on the flow cytometer will not require correction factors due to quenching or changes in extinction coefficient.

DETAILED DESCRIPTION OF THE INVENTION, AND PREFERRED EMBODIMENTS THEREOF

The microbead standards kit useful in the broad practice of the present invention will contain blank, or auto-fluorescent microbeads, and at least two different series of calibrated fluorescent microbead populations, with which to perform the alignment, compensation, and calibration of multi-fluorescence channels of a flow cytometer.

The microbead standards employed in the alignment, compensation, and calibration kit of the invention are highly uniform, having a coefficient of variation (CV) of diameter which is ≦2%. Preferably, such microbead standards are of all the same size, in the range of the cells or particles to be measured, e.g., 2–20 microns in diameter, so as to fall within the forward and right angle dot plot range of the cell or particle samples being measured. If calibration of sizing channels of the flow cytometer is desired, an additional series of microbeads of different calibrated size may be included in the kit to perform the appropriate calibrations, similar to those carried out for the fluorescence intensity channels.

The blank microbeads in the microbeads standards kit of the invention will not carry any fluorescent material. The signal detected in the fluorescence channels of the flow cytometer from such blank microbeads is due to stray light from the optics and/or electronic noise in the instrument. If the samples being measured do not carry out any fluorescent material, their fluorescence signals detected by the instrument should match that of the blank microbeads. This may not be the case, however, with some samples carrying varying amounts of fluorescent materials, e.g., biological cells containing riboflavin, which is fluorescent. When the sample contains such indigenous fluorescent material, the sample is considered to be auto-flourescent. Relatively high levels of auto-flourescence have been observed in hepatic cells and in various cells in culture. When the samples to be measured are auto-fluorescent in character, the microbead standards kit will desirably contain auto-fluorescent microbeads in addition to or in lieu of the aforementioned blank microbeads.

In accordance with the present invention, the blank, or auto-fluorescent, microbead standard in the microbead standards kit must match the fluorescence spectra and intensity of the unlabled, e.g., unstained, samples. Therefore, for the auto-fluorescent microbead standard to match the auto-fluorescent samples, dyes must be associated with the otherwise "blank" microbeads such that they match the excitation and emission spectra of the unlabeled auto-fluorescent samples.

Each series of fluorescent microbeads in the kit will have excitation and emission spectra that match each specific fluorescent dye used to label the samples to be measured on the flow cytometer. Each series of fluorescent microbead standards in the kit will be calibrated in terms of number of equivalent soluble fluorescent molecules of the particular dye. For example, if the samples to be measured are labeled with fluorescein- and phycoerythrin-conjugated antibodies, then a series of fluorescein microbead standards and a series of phycoerythrin microbead standards would be included in the kit. Preferably, the fluorescence intensity range of the microbeads will directly cover that of the samples to be measured, but the microbead standards kit may suitably contain microbeads with which the calibration may be extrapolated to cover the fluorescence intensity range of the sample.

The microbead standards kit of the present invention may also include fluorescent microbead standards which carry combinations of two or more of the dyes to be concurrently used to label the samples being measured. With proper compensation of the flow cytometer, such multilabeled microbeads will be detected in two or more of the respective primary fluorescence channels, so as to simulate individual multilabeled samples. The fluorescence intensities of the microbeads with respect to the individual dyes on the microbead may be selected and provided via appropriate dye incorporation techniques during the formation of the microbead so that their fluorescence intensities are equal or set to specific levels.

The method of use of the microbead standards kit of the invention involves three procedures to ensure that data from multi-fluorescent samples may be accurately obtained from a flow cytometer. These procedures are (i) alignment, (ii) compensation, and (iii) calibration. Although instruments from different flow cytometer manufacturers have their own peculiarities, the following description typifies the general approach to these procedures.

(i) Alignment of a Flow Cytometer

The flow cytometer may be aligned by first choosing the instrument parameters, e.g., excitation wavelength, emission barrier filters, amplifiers (linear or log), and signal gains to be used with the samples to be measured. Then one of the brightest fluorescent microbead standards is used to calibrate the first fluorescence channel F11 of the instrument. Adjustment of the various optical and electronic components of the flow cytometer is then carried out, as directed by the manufacturer, such that the instrument indicates maximum forward and right angle scatter and channel F11 fluorescence intensities with the minimum distribution (% CV) for these microbeads, as measured on dot plots or histograms. Instrument components related to the additional fluorescent channels may then be aligned; this may be accomplished by adjusting the components of these channels to obtain a maximum intensity and minimum distribution while running bright microbeads carrying the dyes that will be used to calibrate those specific fluorescence channels.

(ii) Multi-channel Compensation of a Flow Cytometer

When two or more fluorescent dyes are simultaneously measured with a flow cytometer, the instrument must be compensated to remove spectral overlap in the secondary fluorescence channels. This is accomplished after the fluorescence channels of the instrument are aligned. The blank or, if required, the auto-fluorescent microbeads matching the fluorescence spectra and intensity of the unlabeled sample to be measured, is then run in the flow cytometer in the F11 versus F12 fluorescence channel dot plot or histogram display mode.

Since some microbeads have doublet and triplet components, which can confuse the analysis, gates are placed round the singlet microbead population such that only singlet microbeads register in the fluorescence channels. The PMT voltages and gains then are adjusted such that the signals in each of the fluorescence channels fall close to the origin of the fluorescence intensity measurement scales. Boundary gates may be set for each fluorescent channel such that any signals falling between zero and these gates will be considered non-fluorescent with respect to that particular fluorescence channel.

Next, there is added to the blank microbead population one or more of the fluorescent microbead populations in the calibration series, containing the particular dyes that are used to label the samples to be measured. These additional microbeads will appear along the axis of their respective fluorescence channels and will spill over into areas of positive fluorescence in secondary channels. While running this mixture of microbeads, the compensation circuits of the instrument are turned on and adjusted, as prescribed by the manufacturer, such that the fluorescence signals in the secondary channels are moved between zero and the boundary gate into the non-fluorescence region. An iterative procedure of PMT and compensation circuit adjustments may be required for optimal performance.

As a final check of the multi-channel compensation of the flow cytometer, microbeads carrying combinations of the dyes used to label the samples being measured may be run to determine if they appear in both fluorescence channels as expected.

(iii) Calibration of the Flow Cytometer

Once the alignment and compensation procedures are completed, the fluorescence channels may be calibrated using the series of microbead standards which carry the fluorescent dyes used to label the samples. Without changing any of the instrument settings, microbeads in each series are run separately, or as a mixture, and their peak modal or mean channels are plotted against the calibrated values of the fluorescence intensity for each microbead population in terms of number of equivalent soluble florescent molecules, to provide a calibration plot of the type shown in FIG. 6 hereof. When using a linear amplifier, the plot is made on log-log paper and with a log amplifier, semi-log paper is used. The position peak of the blank microbead on the calibration plots determines the sensitivity of the particular fluorescence channels. The peak position of the auto-fluorescent microbead on the calibration plots determines the threshold fluorescence above which the labeled sample may be measured for the particular fluorescence channel.

The features and advantages of the present invention are more fully shown with respect to the following non-limiting examples, wherein all parts and percentages are by weight, unless otherwise expressly stated.

EXAMPLE I

A population of microbead standards 5.5 microns in diameter and 1.5% coefficient of variation of diameter was synthesized containing 5% glycidyl methacrylate. A portion of these microbeads were impregnated with riboflavin in methanol solution (1% of saturation) to serve as auto-fluroescent microbeads simulating unlabeled cells.

Another portion of the microbeads were reached at pH 9.5 with diaminopropane to provide primary amines with which to covalently bind fluorescein isothiocyanate (FITC). From these microbeads, four fluorescein microbead populations were labeled with increasing amounts of FITC.

Another portion of these glycidyl methacrylate microbeads was reacted with aqueous glycine solution at pH 9.5 to provide carboxyl groups with which to bind four different levels of phycoerythrin via carbodiimide activation. The detailed synthesis of these microbeads and their calibration in terms of equivalent soluble fluorescent molecules is described in U.S. Pat. No. 4,714,682.

EXAMPLE II

A FACScan ™ flow cytometer (Becton Dickinson & Co., Mountain View, Calif.) was used having an air cooled argon laser tuned to an excitation wavelength of 488 nm and fitted with a 520–550 nm bandpass filter on the green fluorescence channel F11 and a 565 nm longpass barrier filter on the red fluorescence channel F12 and with log amplifiers on the fluorescence channels. Count rates were kept to 500 per second. The forward scatter, side scatter, and green F11 channels of the instrument were aligned using the brightest ($2.4 \times 10^5$ equivalent soluble fluorescent dye molecules per microbead) fluorescein (i.e., FITC labeled) microbead. The red F12 channel was then aligned with the brightest ($2.2 \times 10^5$ equivalent soluble fluorescent dye molecules per microbead) phycoerythrin microbead from Example I.

EXAMPLE III

After instrument alignment, as described in Example II, discrimination gates were set around the singlet peak of the auto-fluorescent microbeads from Example I (which matched the fluorescence properties of unstained biological cells) and run with the voltages of the green F11 and red F12 PMT dectors adjusted so that the signals in the dot plot mode fell in the lower left hand corner of the dot plot.

Boundaries were then set on the dot pattern generated from the auto-fluorescent microbeads, to demarcate regions below which non-fluorescent samples would be found equivalent to the auto-fluorescent blank microbeads.

The complete series of fluorescein and phycoerythrin microbead populations were next mixed with the auto-fluorescent blank microbeads and run. The resulting dot patterns indicated a small degree of fluorescent ovelap of the phycoerythrin microbeads in the green F11 channel and a large degree of fluorescent overlap of the fluorescein microbeads in the red F12 channel. The instrument compensation circuits were turned on and adjusted (0.8 F11–% F12 and 24.7 F12–% F11) such that the fluorescence overlapping into secondary fluorescence channels was removed.

EXAMPLE IV

Without changing any settings on the FACScan ™ flow cytometer as set in Example III, the modal peaks of the histograms for each microbead population were plotted on semi-log paper for the respective fluorescence channel since a log amplifier was used. The auto-fluorescent microbead was found to have a fluorescence intensity equivalent to 1,800 equivalent soluble fluorescein molecules in the green F11 channel and 2,400 equivalent soluble phycoerythrin molecules in the red F12 channel indicating the level above which the cells being measured would show fluorescence labeling. Blank microbeds were found to have 1,100 equivalent soluble fluorescein molecules in the green F11 channel and 1,300 equivalent soluble phycoerythrin molecules in the red F12 channel, indicating the sensitivity of the instrument in those channels.

EXAMPLE V

A sample of normal whole blood drawn in ethylene diamine tetraacetate (EDTA) was stained with Leu 3-PE conjugated monoclonal antibody (directed against CD 4 T-cells) and Leu 2a-FITC conjugated monoclonal antibody (directed against CD 8 T-cells). The blood sample was washed twice in PBS and lysed with a lysing reagent from Becton Dickinson to remove the erythrocytes before running on the FACScan ™ flow cytometer. The CD 4 cells were found to have a fluorescence intensity of 70,000 and the CD 8 cells were found to have a phycoerythrin intensity of 133,700 equivalent soluble fluorescent molecules per cell.

While the invention has been described with reference to specific embodiments and compositions, it will be appreciated that numerous modifications, variations, and embodiments are possible, and accordingly all such variations, modifications, and embodiments are to be regarded as being within the spirit and scope of the invention.

What is claimed is:

1. A microbead standards kit for alignment, compensation, and calibration of a flow cytometer for subsequent measurement of a selected fluorescently labeled sample, said kit comprising:
   (a) a population of microbeads characterized by a same fluoresence spectra and fluoresence intensity as a selected fluorescently unlabeled sample prior to the selected fluorescently unlabeled sample being fluorescently labeled to yield a selected fluorescently labeled sample, said microbead population being selected from the group consisting of fluorescently unlabeled microbeads and auto-fluorescent microbeads;
   (b) populations of microbeads which are labeled with at least two fluorescent dyes such that said labeled microbead populations comprise microbeads which are characterized by fluorescence intensity levels registerable in multiple fluorescence channels of a flow cytometer, each same labeled population comprising a series of sub-populations of said labeled microbeads characterized by differing selected levels of fluorescence intensity to substantially encompass a range of fluorescence intensity of said selected fluorescently labeled sample to be measured by a flow cytometer, when said selected fluorescently labeled sample is fluorescently labeled with a same fluorescent dye;
   (c) said microbead populations (a) and (b) being constituted by highly uniform same sized microbeads having a coefficient of variation of diameter of about 2% or less, with said size of said microbeads being substantially equivalent to a size of said selected fluorescently labeled sample to be measured by a flow cytometer; and
   (d) container means enclosing said microbead populations (a) and (b).

2. A microbead standards kit according to claim 1, wherein said highly uniform size microbeads have a diameter in the range of from about 2 to about 20 microns.

3. A microbead standards kit according to claim 1, wherein said microbead population (b) comprises a first sub-population comprising microbeads labeled with a first fluorescent dye, and a second sub-population comprising microbeads labeled with a second fluorescent dye.

4. A microbead standards kit according to claim 1, wherein said microbead population (b) comprises microbeads which are multiply labeled with different fluorescent dyes.

5. A microbead standards kit according to claim 3, wherein said first fluorescent dye is fluorescein, and said second fluorescent dye is phycoerythrin.

6. A microbead standards kit according to claim 4, wherein said different fluorescent dyes comprise fluorescein and phycoerythrin.

7. A microbead standards kit according to claim 3, wherein said first fluorescent dye is Texas Red, and said second fluorescent dye is allophycocyanine.

8. A microbead standards kit according to claim 4, wherein said different fluorescent dyes comprise Texas Red and allophycocyanine.

9. A microbead standards kit according to claim 1, comprising a microbead population (a) of fluorescently unlabeled microbeads.

10. A microbead standards kit according to claim 1, wherein said microbead population (a) comprises auto-fluorescent microbeads.

11. A microbead standards kit according to claim 10, wherein said auto-fluorescent microbeads are labeled with riboflavin.

12. A method of aligning, compensating, and calibrating a flow cytometer comprising multiple fluorescence channels including F11 and F12 fluorescence channels, and forward and right angle scatter channels, a fluorescence excitation source, photomultiplyer tubes and emission barrier filters for said multiple fluorescence channels, and amplifier and gain setting means, for subsequent measurement of a selected fluorescently labeled sample, said method comprising the steps of:

(i) providing a microbead standards kit comprising:
  (a) a population of microbeads characterized by a same fluorescence spectra and fluorescence intensity as a selected fluorescently unlabeled sample prior to the selected fluorescently unlabeled sample being fluorescently labeled to yield a selected fluorescently labeled sample, said microbead population being selected from the group consisting of fluorescently unlabeled microbeads and auto-fluorescent microbeads;
  (b) populations of microbeads which are labeled with at least two fluorescent dyes such that said labeled microbead populations comprise microbeads which are characterized by fluorescence intensity levels registerable in multiple fluorescence channels of a flow cytometer, each same population comprising a series of sub-populations of said labeled microbeads characterized by differing selected levels of fluorescence intensity to substantially encompass a range of fluorescence intensity of said selected fluorescently labeled sample to be measured by a flow cytometer, when said selected fluorescently labeled sample is fluorescently labeled with a same fluorescent dye;
  (c) said microbead populations (a) and (b) being constituted by highly uniform same size microbeads having a coefficient of variation of diameter of about 2% or less, with said size of said microbeads being substantially equivalent to the size of said selected fluorescently labeled sample to be measured by a flow cytometer; and
  (d) container means enclosing said microbead populations (a) and (b);

(ii) running a first population of fluorescent microbeads of said microbead population (b) detectable in said F11 fluorescence channel of said flow cytometer, and aligning and focusing said flow cytometer such that a dot plot or histogram resulting from said first population of microbeads will have a maximum intensity and a minimum distribution in said forward and right angle scatter and F11 fluorescence channels;

(iii) repeating step (ii) with a second microbead population from said microbead population (b) labeled with a different fluorescent dye detectable in said F12 fluorescence channel of said flow cytometer;

(iv) running said microbead population (a) on said flow cytometer, and said adjusting fluorescence channel photomultiplyer tube voltages and gains of said flow cytometer to position a resulting dot plot or histogram near an origin of an axis of each said fluorescence channel, and setting boundary gates in each said fluorescence channel to indicate fluorescence intensity of said microbead population (a);

(v) mixing said first and second fluorescent microbead population used in steps (ii) and (iii) with the microbead population (a) to form a fluorescent microbead adjustment mixture;

(vi) running the fluorescent microbead adjustment mixture on said flow cytometer and adjusting compensation circuits of said flow cytometer so that a fluorescence signal from each of the said first and second microbead populations registers as positive fluorescence in a respective primary fluorescent channel and as non-fluorescent, matching an intensity level of said microbead population (a) in all other secondary fluorescence channels;

(vii) running on said flow cytometer microbead populations (b) labeled with fluorescent dyes, without changing any flow cytometer settings, to determine a modal peak channel of a series of microbead populations labeled with fluorescent dyes at varying specific levels of fluorescent intensity;

(viii) constructing a calibration plot of equivalent soluble fluorescent dye molecules per microbead as a function of fluorescence intensity channel of said flow cytometer;

(ix) running said fluorescently unlabeled microbead population (a) on said flow cytometer and determining a position of a modal peak thereof for each said fluorescence channel to determine a sensitivity of each said fluorescence channel of said flow cytometer; and (x) determining on said calibration plot a position of a modal peak of the auto-fluorescent microbead population (a) for each said fluorescent channel to indicate a threshold above which fluorescence intensity of said selected fluorescently labeled sample may be measured by the said fluorescence channels of said flow cytometer.

13. A method according to claim 12, comprising repeating step (ii) for each of said fluorescent channels of said flow cytometer.

14. A method according to claim 12, further comprising running on said flow cytometer microbead populations (b) labeled with at least two fluorescent dyes to confirm capability of said flow cytometer for simultaneous fluorescence detection for samples labeled with a corresponding combination of said fluorescence dyes.

15. A method according to claim 12, wherein said fluorescent dye comprises at least one member of the group consisting of fluorescein, phycoerythrin, Texas Red, and allophyacocyanine.

16. A method according to claim 12, wherein said microbead population (a) comprises microbeads labeled with riboflavin at sufficient concentration to match fluorescence spectra and fluorescence intensity of said sample.

17. A method according to claim 12, comprising constructing said calibration plot as a log-log plot, wherein said amplfier means of said flow cytometer is a linear amplifier.

18. A method according to claim 12, wherein said calibration plot is constructed as a semi-log plot, and said amplifier means of said flow cytometer is a log amplifier.

19. A method of analyzing a selected sample on a flow cytometer, comprising measuring said sample on said flow cytometer after said flow cytometer has been aligned, compensated, and calibrated in accordance with the method of claim 12.

20. A method according to claim 19, wherein said sample comprises T-cells.

21. A method according to claim 20, wherein said T-cells are stained with fluorescent dyes comprising fluorescein isothiocyanate and phycoerythrin.

22. A method according to claim 21, wherein said T-cells are stained with said fluorescent dyes conjugated with monoclonal antibodies to said T-cells.

* * * * *

UNITED STATES PATENT AND TRADEMARK OFFICE
CERTIFICATE OF CORRECTION

PATENT NO. : 4,857,451

DATED : August 15, 1989

INVENTOR(S) : Abraham Schwartz

It is certified that error appears in the above-identified patent and that said Letters Patent is hereby corrected as shown below:

The title page showing the illustrative figure should be deleted to appear as per attached title page showing the illustrative figure which has been rotated 90° counterclockwise.

Signed and Sealed this

Twelfth Day of June, 1990

*Attest:*

HARRY F. MANBECK, JR.

*Attesting Officer*      *Commissioner of Patents and Trademarks*

United States Patent [19]

Schwartz

[11] Patent Number: 4,857,451
[45] Date of Patent: Aug. 15, 1989

[54] METHOD OF COMPENSATING AND CALIBRATING A FLOW CYTOMETER, AND MICROBEAD STANDARDS KIT THEREFOR

[75] Inventor: Abraham Schwartz, Durham, N.C.

[73] Assignee: Flow Cytometry Standards Corporation, Research Triangle Park, N.C.

[21] Appl. No.: 128,786

[22] Filed: Dec. 4, 1987

Related U.S. Application Data

[63] Continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^4$ .................. G01N 53/00; G01N 31/00
[52] U.S. Cl. ................................ 435/7; 436/10; 424/3
[58] Field of Search ............. 436/10, 19, 800; 435/7; 526/273, 320, 328, 328.5, 181, 201, 88, 332; 424/3; 523/202, 205, 201, 223; 525/327.3, 330.3, 330.5, 343, 351, 379, 382, 384, 284, 350; 524/461, 464, 558, 853, 458; 428/407, 516, 402; 252/301.35, 408.1; 521/60, 149; 250/461.2; 356/39

[56] References Cited

U.S. PATENT DOCUMENTS

| | | | |
|---|---|---|---|
| 4,609,689 | 9/1986 | Schwartz et al. | 526/909 |
| 4,694,035 | 9/1987 | Kasai et al. | 526/201 |
| 4,698,262 | 10/1987 | Schwartz et al. | 526/201 |
| 4,699,826 | 10/1987 | Schwartz et al. | 526/201 |
| 4,699,828 | 10/1987 | Schwartz et al. | 526/201 |
| 4,714,682 | 12/1987 | Schwartz | 436/10 |
| 4,751,188 | 6/1988 | Valet | 436/10 |

Primary Examiner—Barry S. Richman
Assistant Examiner—T. J. Wallen
Attorney, Agent, or Firm—Steven J. Hultquist

[57] ABSTRACT

A kit of highly uniform microbead standards for flow cytometer alignment, compensation, and calibration, comprising a blank and/or auto-fluorescent microbead population, together with two or more series of calibrated microbead populations which match the fluorescence spectra of labeled samples to be measured on the flow cytometer. Also disclosed is a corresponding method to align, compensate, and calibrate a flow cytometer so as to make measurements on corresponding samples comparable and independent of the specific instrument and instrument settings.

22 Claims, 2 Drawing Sheets